United States Patent [19]

Chiu et al.

[11] Patent Number: 4,670,605

[45] Date of Patent: Jun. 2, 1987

[54] PROCESS AND CATALYST FOR THE CONVERSION OF CYCLOHEXANOL TO CYCLOHEXANONE

[75] Inventors: Horn-Ming Chiu, Hsinchu; Min-Hon Rei, Taipei, both of Taiwan

[73] Assignee: Industrial Technology Research Institute, Hsinchu, Taiwan

[21] Appl. No.: 740,179

[22] Filed: May 31, 1985

[51] Int. Cl.$^4$ ............................................. C07C 45/51
[52] U.S. Cl. .................................................. 568/361
[58] Field of Search ..................... 568/361, 363, 403

[56] References Cited

U.S. PATENT DOCUMENTS

| | | | |
|---|---|---|---|
| 1,892,011 | 12/1932 | Sandkuhl | 568/361 |
| 1,892,766 | 1/1933 | Jaeger | 568/361 |
| 2,039,543 | 5/1936 | Lorang | 568/403 |
| 2,338,445 | 1/1944 | Laucht | 568/361 |
| 2,377,412 | 6/1945 | Frey | 568/361 |
| 2,472,493 | 6/1949 | Schneider et al. | 568/361 |
| 2,586,694 | 2/1952 | Mottern | 568/403 |
| 2,701,264 | 2/1955 | Deahl et al. | 568/403 |
| 3,374,270 | 3/1968 | Hausen et al. | 568/363 |
| 3,560,406 | 2/1971 | Juguin | 568/361 |

FOREIGN PATENT DOCUMENTS

| | | | |
|---|---|---|---|
| 947112 | 1/1964 | United Kingdom | 568/361 |
| 978909 | 12/1982 | U.S.S.R. | 568/361 |

*Primary Examiner*—James H. Reamer
*Attorney, Agent, or Firm*—Bert J. Lewen; Henry Sternberg

[57] ABSTRACT

A catalyst and a process to convert commercial cyclohexanol feed to cyclohexanone at a relatively low temperature at stable conversion levels for long periods of operation. This process and catalyst allow operation in the presence of water and high boiling side products. The process features high conversion efficiency and low by-product formation, by use of an improved CuO-ZnO catalyst promoted with an alkali-metal compound such as sodium carbonate. The catalyst is stable in the presence of water and heavy end products in the feedstock (up to 13%). The presence of water rejuvenates the catalyst, increases the conversion and decreases the phenol content in the product mixture.

7 Claims, 3 Drawing Figures

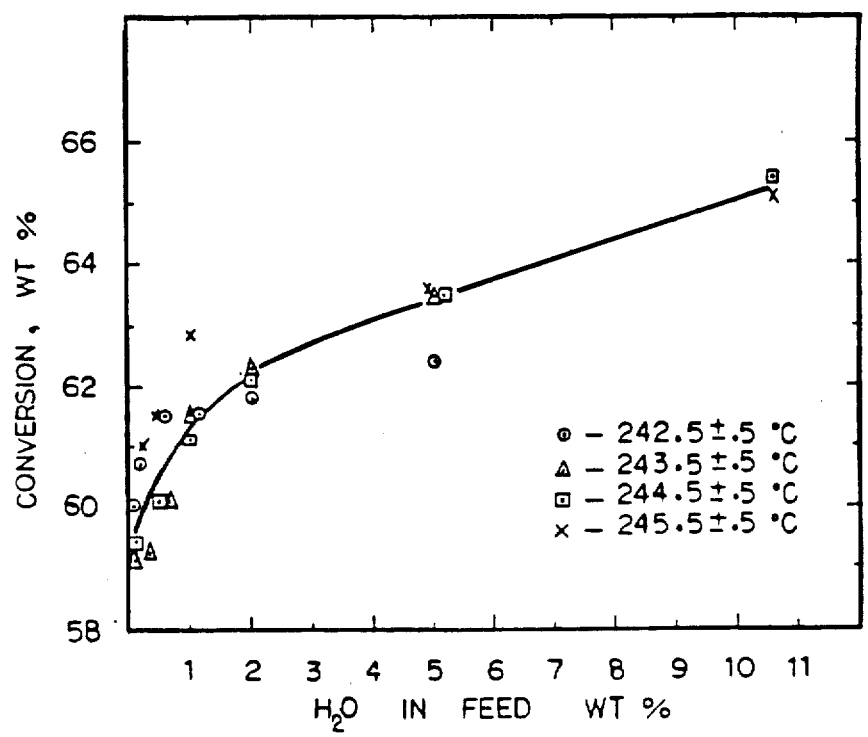
FIG. 1 THE EFFECT OF WATER ON CONVERSION

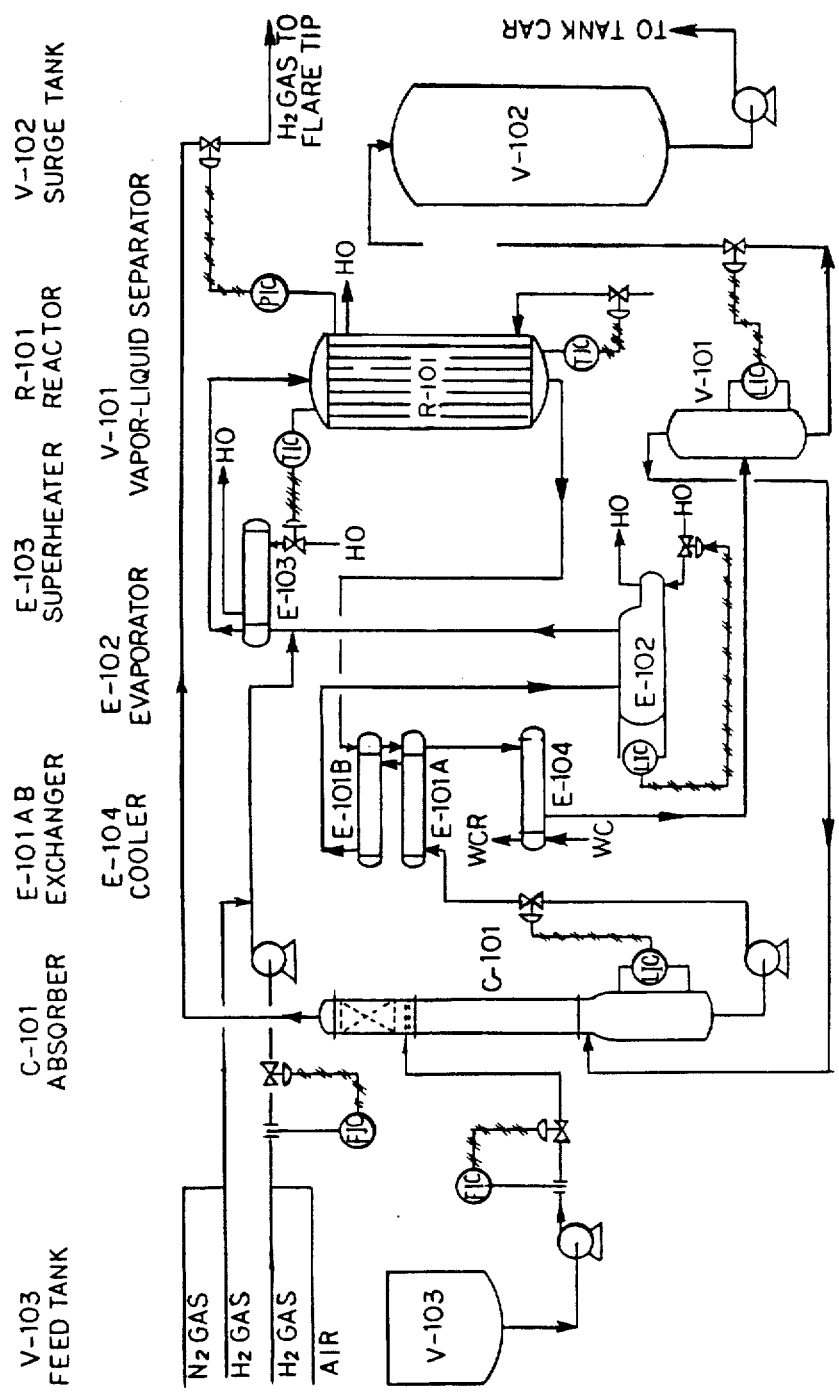
FIG. 2 FLOW DIAGRAM OF PLANT FOR CYCLOHEXANOL CONVERSION

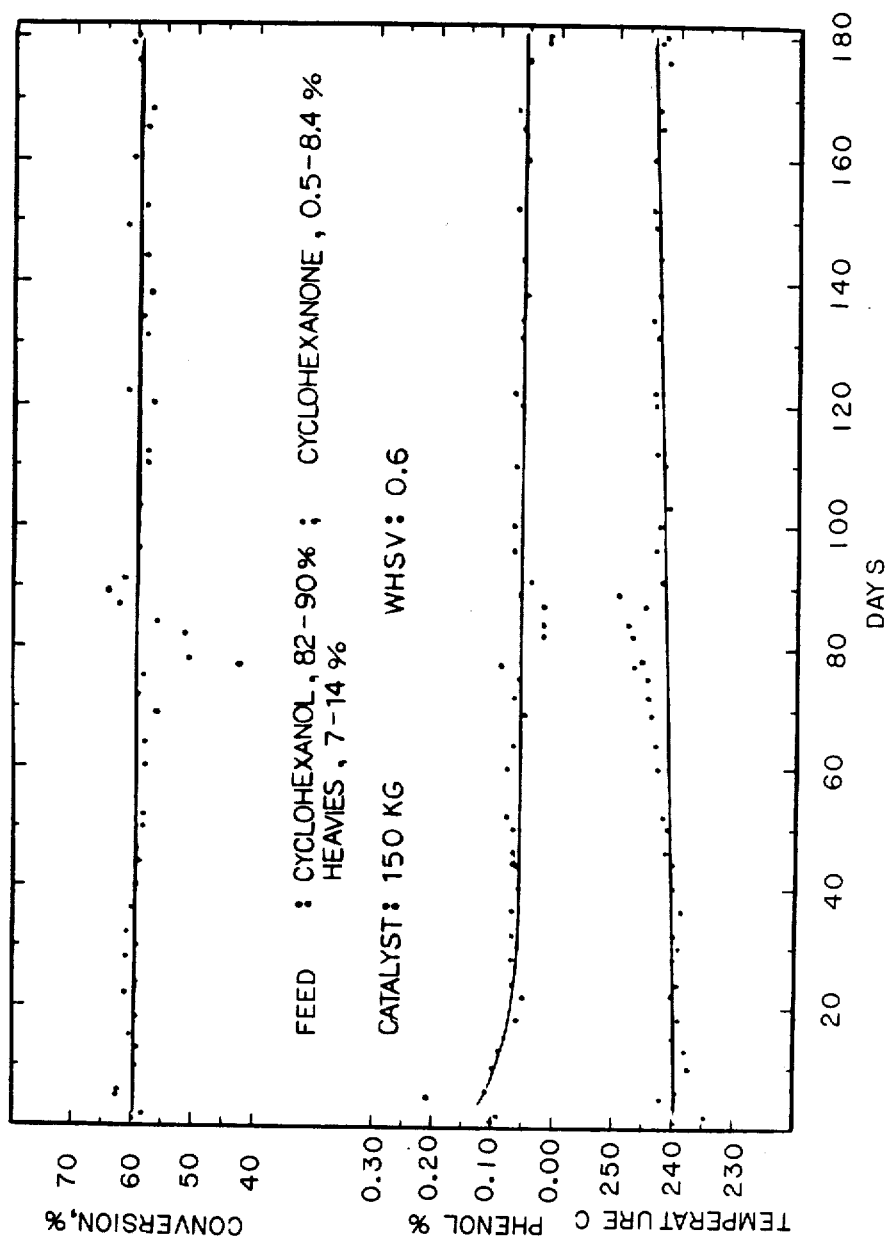
FIG. 3 AGING TEST OF CATALYST

PROCESS AND CATALYST FOR THE CONVERSION OF CYCLOHEXANOL TO CYCLOHEXANONE

BACKGROUND OF THE INVENTION

1. Field of the Invention

A catalytic process, including a new catalyst, for the catalytic dehydrogenation of cyclohexanol to cyclohexanone.

2. Description of the Prior Art

Industrially, cyclohexanol is converted to cyclohexanone in the presence of a copper catalyst at temperatures of 220° to 260° C. or 350° to 450° C. The low temperature conversion, in the prior art results in low throughput, and the catalyst may be subject to deactivation by the water produced as a by-product of the reaction. The hydrolysis of the catalyst by the water vapor may also fracture the catalyst and build up the pressure drop. A high temperature conversion catalyst enables nearly complete conversion of cyclohexanol to cyclohexanone; however, this often causes undesired production of phenol and cyclohexene, resulting in an efficiency loss.

Copper oxide-zinc oxide catalysts have been reported in several literature and patent references namely, A. Sputa et al, Czechoslovakia Patent 151,166, Dec. 15, 1973 (CA 80: 145,560); Mitsubishi Chemical Industries Co., Ltd., Japanese Kokkyo Koho 80/136,241, Oct. 23, 1980 (CA 94: 156,414); R. I. Belskaya et al., Inst. Fiz., Org. Khim., Minsk, USSR 1981 (CA 96: 103,707); N. P. Emelyanov et al., Dokl. Akad. Nauk Beloruss. SSR 11(3), 233 (RUSS) 1967 (CA 67: 108,283); N. P. Emelyanov et al., Dokl. Akad. Nauk Beloruss., French Pat. No. 2,030,602, Nov. 13, 1970 (CA 75: 48,542), U.S. Pat. No. 3,652,460, Mar. 28, 1972 (CA 76: 145,400) V. S. Komarov et al., Dokl. Akad. Nauk Beloruss USSR Pat. No. 660,701, May 5, 1979 (CA 91: 39,009); V. S. Komarov et al., Dokl. Akad. Nauk Beloruss. SU 978,909, Dec. 7, 1982 (CA 98: 160,232). Disclosures relative to adding water to the feedstock to enhance selectivity and conversion rate appear in Ruhrchemie AG British Pat. No. 1,444,484 and UBE Industries, Ltd. Japanese Patent Kokai 73/29,742, Apr. 19, 1973.

As mentioned above, the known types of copper oxide-zinc oxide catalysts often bring about the formation of undesirable cyclohexene and phenol. Accordingly, some of these were promoted with calcium, barium-ruthenium metals to modify the catalytic properties.

SUMMARY OF THE INVENTION

1. Objects of the Invention

It is an object of the present invention to provide an improved process for the catalytic dehydrogenation of cyclohexanol to cyclohexanone.

Another object is to provide an improved catalyst for the conversion of cyclohexanol to cyclohexanone.

A further object is to provide an improved low temperature catalytic conversion process for the dehydrogenation of cyclohexanol to cyclohexanone, in which the conversion is improved and by-product formation is inhibited.

An additional object is to provide such a process and catalyst in which the conversion is improved, by use of an improved catalyst which is stable and resistant in the presence of water and heavy end products in the feedstock (up to 13%).

Still another object is to provide such a process in which the CuO—ZnO catalytic agent is promoted by an alkali metal compound such as sodium carbonate, bicarbonate or carboxylate.

Still a further object is to provide an improved catalyst for and a process which is compatible with water.

These and other objects and advantages of the present invention will become evident from the following description.

2. Description of the Invention

It has been discovered that a catalyst composed of copper oxide and zinc oxide promoted with an alkali metal compound such as sodium carbonate is capable of producing high conversions of cyclohexanol to cyclohexanone at a relatively low reaction temperature, without a large increase of phenol by-product and aldol condensation products.

The catalyst is not only stable thermally during the operation, but is also resistant to the poisonous effect of large amounts of water and high boiling products which are present in industrial cyclohexanol feedstock.

Furthermore, two beneficial effects of water have been found by using the subject catalyst in a large scale pilot plant test for converting cyclohexanol to cyclohexanone. Firstly, the incorporation of the proper amount of water unexpectedly increases the conversion and decreases the phenol content in the reaction product. Secondly, an increase of catalyst activity is observed by the addition of a large amount of water for a short period, and this increase of activity was kept unchanged even after the water concentration decreased to the normal level. This rejuvenation effect of water occurred repeatedly in plant tests to maintain a constant level of conversion without the need to significantly increase the reaction temperature.

The product cyclohexanone is used, inter alia, in the manufacture of caprolactum, and constitutes a caprolactum precursor. The process features high conversion efficiency and low by-product formation, due to the improved catalyst of CuO—ZnO promoted by an alkali metal compound such as sodium carbonate. The catalyst is stable and resistant to water and heavy end products in the feedstock (up to 13%). The presence of water serves to rejuvenate the catalyst, and to increase the conversion and to decrease the phenol content in the product mixture. The modified CuO—ZnO catalyst retains its activity, is fast, and selective. The process achieves a selectivity of from 97 to 99% at a conversion level of 50 to 60%.

The copper oxide-zinc oxide catalyst is promoted with a small but effective amount of alkali metal compound. The alkali metal compound will generally be present in the range of about 0.05 to 16 wt%, preferably 0.1 to 5.0 wt%. The alkali metal compound is typically a salt such as sodium carbonate, bicarbonate or alkali metal salt of an organic acid, e.g., acetate, citrates, naphthanate or octoate, which decomposes to the oxide slowly upon heating. The alkali metal may be sodium, potassium, lithium, cesium or rubidium.

With the catalyst of the invention the presence of water has a salutary effect. Generally, the feedstream may contain up to about 10 wt% of water, and up to about 14 wt% of regular industrial side products. Typically, the catalyst, when partially deactivated, is rejuvenated by the incorporation of water in the process environment. The conversion usually takes place in a tube and shell reactor, at an elevated temperature in the range of about 200° C. to 320° C., preferably 220° C. to 260° C. The space velocity in the reactor is generally in the range of about 0.1 to 3.0, preferably, from 0.5 to 1.5.

BRIEF DESCRIPTION OF THE DRAWINGS

FIG. 1 shows the effect of water in the cyclohexanol feed on the conversion to cyclohexanone over the promoted copper oxide-zinc oxide catalyst of the invention;

FIG. 2 is a process flow diagram of the cyclohexanol conversion system; and

FIG. 3 shows the results of a continuous aging test using the catalyst in the process of the invention.

DETAILED DESCRIPTION OF THE PREFERRED EMBODIMENTS

Following are Examples which illustrate various aspects of the invention, as well as comparative Examples showing the advantages of the present catalyst.

EXAMPLE 1

The catalyst of the invention is prepared as follows:

Zinc nitrate trihydrate (244 g) and copper nitrate trihydrate (483 g) are dissolved in distilled water (1500 ml) at 25° C. The solution is rapidly agitated while 10% ammonium bicarbonate solution (3000 ml) is added over a period of 30 minutes at 25° C. Agitation is continued for 30 minutes. The slurry is filtered, washed with distilled water (1500 ml), and the filter cake dried at 110° C. for 4 hours. After drying, the cake is calcined at 400° C. for 2 hours.

After cooling, sodium carbonate (0.76 g) is added to the calcined product with sufficient distilled water to produce a paste. The paste is dried and shaped into tablets (6 mm O.D. *3 mm H). The BET surface area is found to be 40 m$^2$/g. Typically, the catalyst is initially reduced with hydrogen and has a BET surface area of about 42 m$^2$/g, a pore volume of 0.23 cc/g, a bulk density of 1.15 g/cc, and a side crush strength (dead weight load) of 7.3 kg (minimum, 6 kg) when in a fresh condition, and 8.3 kg (minimum, 4 kg) after 180 days onstream.

EXAMPLE 2

In a one inch (ID) tubular reactor, cyclohexanol is converted to cyclohexanone at a weight hourly space velocity, (WHSV) of 0.6. The effect of molar ratio of copper oxide to zinc oxide on catalyst activity is shown in Table 1.

TABLE 1

| Molar ratio of CuO/ZnO | Temperature, °C. | Conversion, % |
|---|---|---|
| 2.0 | 214 | 36 |
|  | 228 | 40 |
| 0.5 | 212 | 42 |
|  | 218 | 47 |

The results shown in the above table are for steady state operation after eight hour runs.

EXAMPLE 3

As in Example 2, the copper oxide-zinc oxide catalyst is modified with different amounts of sodium carbonate by an impregnation method. The effect of sodium level on the activity of catalyst is shown in Table 2.

TABLE 2

| Na$_2$CO$_3$ in CuO—ZnO (½) % by weight | Reaction time, Hr | | | |
|---|---|---|---|---|
| | 8 | | 50 | |
| | Temp °C. | Conv. % | Temp. °C. | Conv. % |
| 16 | 214 | 41 | 222 | 27 |
| 5 | 216 | 45 | 224 | 51 |
| 1.7 | 216 | 47 | 224 | 54 |
| 0.34 | 213 | 40 | 226 | 51 |
| 0 | 212 | 42 | 218 | 47 |

EXAMPLE 4

As in Example 2, a copper oxide-zinc oxide catalyst is promoted with a small amount of Group 1A metals by the impregnation method. The effect of Group 1A metals on the conversion of cyclohexanol to cyclohexanone is shown in Table 3.

TABLE 3

| Catalyst | Temp °C. | WHSV | Conversion % |
|---|---|---|---|
| CuO/ZnO (½) | 280 | 1.0 | 82 |
| CuO/ZnO (½) + 0.2% Na | 280 | 1.0 | 87 |
| CuO/ZnO (½) + 0.2% Rb | 280 | 1.0 | 88 |
| CuO/ZnO (½) + 0.2% Cs | 280 | 1.0 | 83 |
| CuO/ZnO (½) + 0.2% K | 217 | 0.6 | 39 |

EXAMPLE 5

As in Example 2, a copper oxide-zinc oxide catalyst is promoted with 1% sodium and with 1% barium, respectively, by the impregnation method. The results for the reactions at 235° C. and 0.6 WHSV are shown in Table 4. The differences between an alkaline metal and an alkaline earth promoted catalyst are also shown.

TABLE 4

| Catalyst | % Conversion on Cyclohexanol | % Selectivity to Cyclohexanone | ppm Phenol in Product |
|---|---|---|---|
| CuO/ZnO (½) + 1% Na | 58 | 100 | 390 |
| CuO/ZnO (½) + 1% Ba | 56 | 99 | 1600 |

EXAMPLE 6

6 g of CuO/ZnO catalyst modified with 0.2 wt% Zr (prepared by impregnation of 0.565 g Zr(NO$_3$)$_2$.2H$_2$O on 96.28 g of CuO/ZnO catalyst) was used to convert cyclohexanol to cyclohexanone at 300° C. at 1.0 WHSV. The products were found to contain 62% of cyclohexanone, 32% of 2-cyclohexyl-cyclohexanone and 5% of phenol. The conversion was calculated to be 70 mol%.

EXAMPLE 7

The interaction of sodium carbonate on copper oxide-zinc oxide and water in the cyclohexanol feed was determined at 215° C. Table 5 shows that adding water alone is not always beneficial. Only when water was added with a specific catalyst, viz, copper oxide-zinc oxide promoted by sodium carbonate, was a better conversion and lower by-product formation obtained.

TABLE 5

| Catalyst % Na$_2$CO$_3$ by weight | % H$_2$O in feed | % Conversion | ppm phenol in product |
|---|---|---|---|
| 0 | 0 | 38.5 | 1400 |
| 0.2 | 0 | 40.1 | 600 |

TABLE 5-continued

| Catalyst % Na$_2$CO$_3$ by weight | % H$_2$O in feed | % Conversion | ppm phenol in product |
|---|---|---|---|
| 0 | 2 | 34.4 | 900 |
| 0.2 | 2 | 41.1 | 500 |

EXAMPLE 8

As in Example 2, cyclohexanol feed containing different amounts of water was converted to cyclohexanone over promoted copper oxide-zinc oxide at 242°–245° C. The results are shown in FIG. 1.

EXAMPLE 9

In a pilot plant reactor composed of 103 carbon steel tubes of 1.5 BWG*6 ft, cyclohexanol, (WHSV=0.6, T=240° C., P=1.7 kg/cm$^2$ abs.) was converted to cyclohexanone at 60% constant conversion level. The flow diagram of the conversion system and the results of a continuous test for 180 days are shown in FIG. 2 and FIG. 3.

EXAMPLE 10

In FIG. 3 of Example 9, the partially deactivated catalyst, after 87 days, was rejuvenated with 10% water in the cyclohexanol feed for 3 days. The results in Table 6 show that adding the proper amount of water to the feedstock will restore the conversion rate and rejuvenate partially deactivated catalyst. The data also show that withdrawing water is not required, for it will not cause a detrimental effect to the catalyst. It is known that adding water to a commercial copper-magnesium dehydrogenation catalyst often leads to the hydrolysis of the catalyst.

TABLE 6

| Time days | Temp. °C. | Water[1] in feed % | Conversion[2] % | Phenol in product % |
|---|---|---|---|---|
| 78 | 246 | 0.26 | 50.9 | 0.05 |
| 79 | 246 | 0.26 | 55.2 | 0.05 |
| 80 | 246 | 0.26 | 57.0 | 0.03 |
| 81 | 247 | 0.26 | 55.0 | 0.03 |
| 82 | 247 | 0.31 | 51.4 | 0.02 |
| 83 | 248 | 0.31 | 55.0 | 0.02 |
| 84 | 248 | 0.31 | 56.0 | 0.02 |
| 85 | 248 | 0.31 | 55.0 | 0.02 |
| 86 | 246 | 0.50 | 59.2 | 0.02 |
| 87 | 245 | 1.00 | 60.4 | 0.02 |
| 88 | 246 | 10.50 | 64.8 | 0.02 |
| 89 | 245 | 10.50 | 64.7 | 0.06 |
| 90 | 246 | 10.50 | 68.2 | 0.07 |
| 91 | 243 | 1.00 | 61.5 | 0.04 |
| 92 | 242 | 0.20 | 59.2 | 0.04 |
| 93 | 243 | 0.20 | 59.2 | 0.04 |
| 94 | 242 | 0.60 | 59.2 | 0.04 |
| 95 | 242 | 0.60 | 58.6 | 0.07 |
| 96 | 243 | 0.60 | 59.2 | 0.07 |
| 97 | 243 | 0.10 | 59.2 | 0.06 |

[1]Cyclohexanol feed contains 84 to 89% of cyclohexanol and 3 to 5% of cyclohexanone.
[2]Reaction selectivity on cyclohexanone ranged from 96 to 98% throughout the test.

EXAMPLE 11

While it is generally known to add water to the cyclohexanol feedstock to enhance selectivity and conversion rate, there are differences between its use in the present invention and existing prior art. For example, in British Pat. No. 1,444,484, a patent granted to Ruhrchemie AG, water was added to feedstock to give a higher selectivity. The catalyst used was copper, whereas in the present invention a copper oxide zinc oxide catalyst promoted by sodium carbonate is used. In a patent granted to Ube Industries, Ltd. (Japan Kokai 73/29,742), 2% of water was added to feedstock for 48 hours after the conversion rate deteriorated to 70% after 150 days. By adding water, the conversion rate was restored to 80%. In comparing this prior art with the present invention, differences, shown in Table 7, are apparent.

TABLE 7

|  | Conversion temperature | Catalyst used | Withdrawal of water |
|---|---|---|---|
| Japan Kokai | 370–380° C. High temperature process | ZnO—CaO (1:1 mol) a catalyst that is inactive under lower temperatures | Immediate withdrawal of water after 48 hours, or detrimental effect will occur to catalyst |
| Present invention | 220–260° C. Low temperature process | Copper oxide-zinc oxide promoted by sodium carbonate | Withdrawal of water not required |

What is claimed is:

1. A low temperature process for the catalytic dehydrogenation of cyclohexanol to cyclohexanone which comprises: contacting, at a temperature of from 200° to 320° C. and at an hourly space velocity of from 0.1 to 3.0, a feed stream containing cyclohexanol and up to 10 wt. % water and up to 14 wt. % industrial by-products with a catalyst consisting essentially of copper oxide and zinc oxide promoted with from 0.05 to 16 wt. % of an alkali metal compound, said compound being capable of decomposing to the oxide upon heating, and recovering an effluent containing cyclohexanone.

2. The process of claim 1 wherein the elevated temperature is from about 220° to 260° C.

3. The process of claim 1 wherein the alkali metal compound is an alkali metal salt.

4. The process of claim 3 wherein the alkali metal salt is sodium carbonate.

5. The process of claim 1 wherein the alkali metal is selected from the group consisting of sodium, potassium, cesium, and rubidium.

6. The process of claim 1 wherein the weight percent is from about 0.1 to 5.0%.

7. The process of claim 1 wherein the catalyst, when partially deactivated, is rejuvenated by the incorporation of water in the process environment.

* * * * *

UNITED STATES PATENT AND TRADEMARK OFFICE
CERTIFICATE OF CORRECTION

PATENT NO. : 4,670,605
DATED : Jun. 2, 1987
INVENTOR(S) : Horn-Ming Chiu and Min-Hon Rei It is certified that error appears in the above-identified patent and that said Letters Patent is hereby corrected as shown below:

Claim 6, line 1: after "%" insert --of the alkali metal compound--.

Signed and Sealed this

Twenty-eighth Day of June, 1988

Attest:

DONALD J. QUIGG

*Attesting Officer*      *Commissioner of Patents and Trademarks*